April 12, 1960 C. H. FISCHER Plant Pat. 1,934
GLADIOLUS PLANT
Filed June 29, 1959
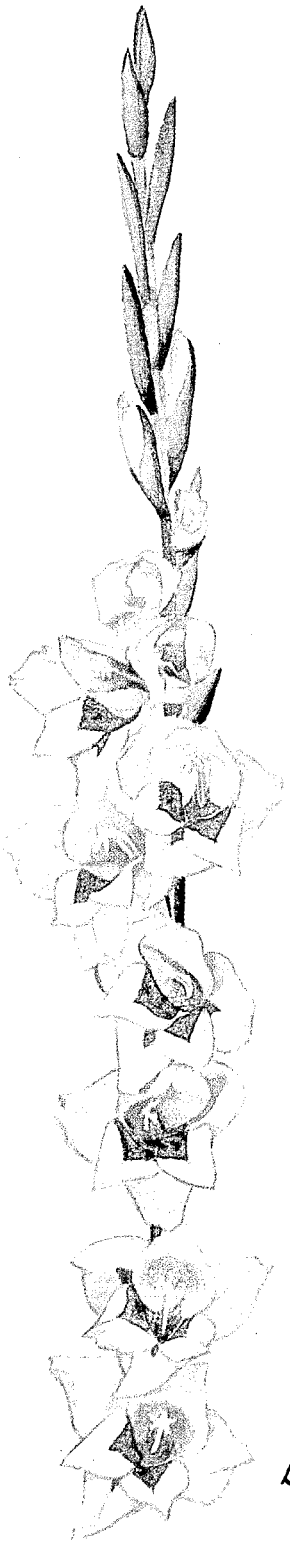
INVENTOR
CARL H. FISCHER
by Lamont Johnston
ATTORNEY United States Patent Office Plant Pat. 1,934
Patented Apr. 12, 1960

1,934

GLADIOLUS PLANT

Carl H. Fischer, St. Charles, Minn., assignor to Selected Glads, Inc., New Albany, Ind., a corporation of Tennessee Application June 29, 1959, Serial No. 823,791

1 Claim. (Cl. 47—60)

My present invention relates to a new and improved variety of gladiolus plant and is notable particularly for its petite size and striking color contrast. I have identified this new variety as seedling No. 253–54 in my breeding work.

To the best of my knowledge, this new variety is the result of a cross between the varieties Caribbean (Plant Patent No. 1,654) and a seedling, unnamed and unpatented, Caribbean being the seed parent and the unknown seedling the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proved to be permanently fixed.

The illustration, made a part of this application, shows a single bloom spike of this new variety, reduced in size, and is as nearly true to color as it is possible to depict. The illustration shows the shape and symmetry of the spike as well as the striking color contrast.

In the following detailed description, color plate references are to the "Horticultural Colour Chart," by the British Colour Council. Where there are other references to color, the ordinary dictionary meanings of the terms are intended.

*The plant*

Growth: Very vigorous, averaging 36 inches in height. Propagates readily.

Blooming: Each spike opens from 7 to 9 three and one-half inch flowers at one time. Successive blooms open, totalling an average of 17 to 18 florets to each spike. The variety is an early bloomer, blooming on the average in 75 to 80 days from large bulbs.

Stems: Stright; stiff. Diameter at base is ½" to ¾".

Foliage: Deep green, average leaf is 1½ inches wide and the plant is 18 inches high.

Disease resistance: This variety is very resistant to disease. It has been found resistant to Sclerotina dry rot, Septoria leaf spot and Fusarium yellows to which some other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases, whereas this variety remained healthy and unaffected.

Corms: Unusually healthy and smooth for varieties of this color group. Flesh of bulb is Indian Yellow 6/2. Average 1½" in diameter from adult plants.

*The flower*

Spike: Sixteen to 18 inches, slender, has 17–18 buds and opens 3–4 flowers the first day, following which 7 to 9 are open at one time until all have opened.

Bud:

*Size.*—Opening buds are 1½ to 2 inches long.

*Opening.*—8 to 9 show color at one time, 3–4 opening the first day.

Flower:

*Arrangement.*—The florets are gracefully arranged in a somewhat double-row fashion and all face in the same direction.

*Size.*—Lower blooms average 3½ inches across when permitted to bloom on the plant in the field. Upper blooms are progressively smaller.

*Form.*—Wide open; recurved and not ruffled. 6 petals; 3 outer petals are larger than the three inner petals. Upper inside petal is slightly hooded.

*Keeping qualities.*—Keeps and opens well.

Petals:

*Shape.*—Petals are plain, oval and slightly recurved.

*Size.*—Three outer petals are 1½ to 1¾ inches from calyx to tip. 3 inner petals are 1¼ to 1½ inches from calyx to tips.

*Aspect.*—Substance is moderately heavy; surface is smooth and plain at the edges.

*Fragrance.*—None.

*Color.*—The largest area of the flower is Lobelia Blue 41/3. The blotch is Pansy Violet 033. The blotch covers the inner area of the three lower petals.

Reproductive organs:

*Stamens.*—Medium, light violet.

*Pistils.*—Three-pronged, extending about the same distance as the stamens. Cream.

*Comparisons*

My new variety resembles Caribbean (Plant Patent No. 1,654) more than any other variety, but differs from it principally as follows:

(1) My variety is much smaller than Caribbean.
(2) My variety is plain-petalled; Caribbean is ruffled.
(3) My variety has a larger, deeper colored blotch.
(4) My variety has a cleaner color than Caribbean.
(5) My variety has a greater contrast between the main color and the blotch.

Having thus disclosed my invention, I claim:

The new and distinct variety of gladiolus plant, substantially as herein shown and described, characterized by its vigorous growth, its sharp, contrasting colors, the clean color and simplicity of form and petite size.

No references cited.